United States Patent
Cascone

(10) Patent No.: US 7,892,480 B2
(45) Date of Patent: Feb. 22, 2011

(54) DENTAL PROSTHESIS METHOD AND ALLOYS

(75) Inventor: Paul J. Cascone, Del Mar, CA (US)

(73) Assignee: The Argen Corporation, San Diego, CA (US)

( * ) Notice: Subject to any disclaimer, the term of this patent is extended or adjusted under 35 U.S.C. 154(b) by 925 days.

(21) Appl. No.: 11/627,079

(22) Filed: Jan. 25, 2007

(65) Prior Publication Data

US 2007/0113707 A1 May 24, 2007

Related U.S. Application Data

(60) Division of application No. 10/846,314, filed on May 14, 2004, now Pat. No. 7,279,054, and a continuation-in-part of application No. 10/846,314, filed on May 14, 2004, now Pat. No. 7,279,054.

(51) Int. Cl.
B22F 3/105 (2006.01)
B22D 25/00 (2006.01)

(52) U.S. Cl. .................. 419/1; 419/12; 419/26; 29/527.5; 164/58.1

(58) Field of Classification Search .............. 75/247
See application file for complete search history.

(56) References Cited

U.S. PATENT DOCUMENTS

| 3,502,466 A | * | 3/1970 | Vickery ................ 419/27 |
| 4,668,289 A | * | 5/1987 | Langer et al. ............ 75/744 |
| 5,217,685 A | * | 6/1993 | Cook et al. ............. 420/509 |
| 5,853,661 A | | 12/1998 | Fischer |
| 5,922,276 A | | 7/1999 | Cascone |
| 6,126,732 A | * | 10/2000 | Hofmann et al. .......... 106/35 |
| 2002/0004018 A1 | * | 1/2002 | Prasad et al. ........... 420/512 |
| 2002/0013636 A1 | * | 1/2002 | O'Brien ............... 700/118 |
| 2004/0032594 A1 | | 2/2004 | Weber et al. |

FOREIGN PATENT DOCUMENTS

| CA | 2152155 | 8/2005 |
| DE | 4439793 C1 | 10/1995 |
| EP | 0717118 B8 | 6/1996 |
| EP | 0729740 A2 | 3/2000 |
| JP | 56003636 | 1/1981 |
| JP | 07166266 | 6/1995 |
| WO | WO01/55465 | 8/2001 |

| WO | WO2004/101835 | 11/2004 |

OTHER PUBLICATIONS

Otsuka et al, "Dental Gold-Titanium Alloy", Internet Document; Japanese Abstract JP9067628; Published Mar. 11, 1997.
Fisher, "Ceramic Bonding to a Dental Gold-Titanium Alloy", Internet Document; Biomaterials, Mar. 2002., vol. 23, No. 5, pp. 1303-1311.
Fukuhisa et al, "Surface hardened Gol Alloys", (Abstract), Finishing, Sep. 1984, vol. 8, pp. 29-32.
Fisher, "Effect of Small Additions of Ir on Properties of a Binary Au-Ti-Alloy", Dental Materials, Jun. 2002, vol. 18, No. 4, pp. 331-335.
Ott, D, "Effect of Small Additions and Impurities on Properties of Carat Golds", FEM Schwabisch Gmund, Germany, World Gold Council, 1997, pp. 31-34.
Ning, "Alloying and Strengthening of Gold Via Rare Earth Metal Additions", Kumming Institute of Precious Metals, Gold Bulletin, 2001, vol. 34, No. 3, pp. 77-87.
Poliero, "White Gold Alloys for Investment Casting", Leg.Or. s.r.l., Bressavido, Vicenza, Italy, pp. 10-20.
Grimwade, "The 15th Santa Fe Symposium of Jewelry Manufacturing Technology", World Gold Council and the Worshipful Company of Goldsmiths, UK, pp. 18-19.
Daigaku, "Patent Abstracts of Japan, Publication No. 56003636, Date of Publication Jan. 14, 1981".
Derwent Publications, Inc., Mosc Alloys Works, XP-002343511, Database WPI, Jun. 25, 1977, 1 page, Section Ch, Week 197811, London, GB.
Derwent Publications, Inc., Sumitomo Metal Mining XP-002343512, Database WPI, Jul. 14, 1998, 1 page, Section Ch, Week 199738, London, GB.
Derwent Publications, Inc., Ishifuku Kinzoku Kogyo KK XP-002343513, Database WPI, Nov. 30, 1976, 1 page, Section Ch, Week 197703, London, GB.
Kempf et al., Canadian Patent Application No. 2,170,084, filed Feb. 22, 1996, entitled Use of Gold Alloys for Precision Attachments in Dental Technology.
European Patent Search Report dated Sep. 5, 2005 for corresponding International Application No. WO 04090367, in the name of the Argen Corporation, 5 pgs.

* cited by examiner

*Primary Examiner*—Roy King
*Assistant Examiner*—Ngoclan T Mai
(74) *Attorney, Agent, or Firm*—Kauth, Pomeroy, Peck & Bailey LLP

(57) ABSTRACT

Dental prostheses are fabricated as a metallic alloy body by a technique that produces scrap alloy. Suitable gold base alloys have only base metal alloying additions which are more readily oxidized than gold and when combined with the gold can be age hardened. Exemplary metals include titanium, zirconium, yttrium and chromium. Scrap from fabricating a dental prosthesis is melted in air so that the base metals are all oxidized and substantially pure gold is reclaimed for reuse in new alloys.

10 Claims, No Drawings

DENTAL PROSTHESIS METHOD AND ALLOYS

CROSS REFERENCE TO RELATED APPLICATIONS

This application is a division and continuation in part of U.S. patent application Ser. No. 10/846,314, filed May 14, 2004 now U.S. Pat. No. 7,279,054. The subject matter of the parent application is hereby incorporated by reference.

FIELD OF THE INVENTION

This invention relates to preparation of dental restorations or prostheses incorporating gold alloys.

BACKGROUND

For over a century the ancient lost wax method of casting has been used to fabricate dental restorations. The success of this method is due to its simplicity, ease of use, and conservative nature of the process. Utilization of the precious metal used for restorations or prostheses of over 95% is easily obtained by remelting the sprues and button attached to the casting. In order to obtain less than 5% waste, the alloy cannot contain volatile elements or elements that are too readily fluxed into slag so that they are lost while the alloy is molten.

Over the last decade the technology of computer controlled machining or milling, CAD/CAM has increasingly been applied to the fabrication of dental prostheses, in particular those made from ceramics. For the dental laboratory the CAD/CAM process holds the promise of reducing labor expense while maintaining the laboratory's productivity.

The nature of the CAD/CAM operation requires the prosthesis to be milled from a larger body of material. The amount of material in the final product is usually a fraction of the amount of material in the original body. The amount of waste or scrap generated is often on the order of 80 to 90%. The process is cost effective for milling ceramics due to the low intrinsic cost of the ceramic materials. However, such a high proportion of waste is quite intolerable for precious metal alloys. For this reason, the milling process is rarely used for the fabrication of dental prostheses using precious metal. The problem is one primarily of economics.

The nature of the CAD/CAM operation requires that the initial body of material be substantially greater than the finished part. Thus, the user must purchase more alloy than is necessary. While the amount of alloy may be minimized in some cases to reduce cost, the main economic factor is how to handle the waste or scrap from machining.

A few typical dental alloy compositions are:

| | | | | |
|---|---|---|---|---|
| Au | 90 | 75 | 65 | 0 |
| Pt | 6 | 0 | 0 | 0 |
| Pd | 2 | 12 | 26 | 60 |
| Ag | 1 | 10 | 0 | 28 |
| In | .5 | 2 | 8 | 6 |
| Sn | 0 | 2 | 0 | 6 |
| Ir | 0.1 | 0.1 | 0 | 0 |
| Ru | 0 | 0 | 0.1 | 0.2 |
| Color | Yellow | White | White | White |

These alloys and others like them are all designed to be used for the lost wax method of casting. The alloying elements were chosen so that there is little loss of any particular component during the casting process. Using these alloys in a CAD/CAM milling operation however, would not be economical, since the large amount of scrap cannot be readily remelted into another body for re-use. The scrap material must be refined, that is, the scrap material must first be dissolved in acid and then each element retrieved separately. The refining process itself requires specialized equipment and the recovery of the platinum group elements in particular is quite expensive.

Such factors increase the final cost of the finished milled product, making it prohibitively expensive compared to the lost wax method of casting.

Recently there have been demonstrations of making dental prostheses by laser sintering or "rapid prototyping". In this technique an article, such as a dental prosthesis, is built up gradually from powder. Powder is placed in a suitable location on a starting substrate and later on the surface of the part being made. A laser or other high energy beam is focused on a spot with sufficient intensity to bond the particles of the powder to form a sold mass. The intensity of the laser spot may be just enough to soften the particles so that they cohere by solid state diffusion and bonding, or the intensity may be enough to melt a small region of the powder for essentially welding the particles together.

Either way, the laser point of focus is scanned over the geometry desired to gradually build up a part of the final geometry. Rapid prototyping has been used to make one-off or unique products by either forming a replaceable mold in which a metal is cast, or by directly forming the part of cohered or welded powder. Although laser has been the preferred approach, it may also be feasible to use an electron beam instead of a laser beam.

Either way of laser sintering or rapid prototyping to form a dental prosthesis directly from metal powder can result in surplus powder on or around the part being fabricated. This scrap powder of precious metal should be recycled to reclaim the precious metals. This invention addresses the economic issue of recycling the scrap from milling or other fabrication technique by providing selected alloying additions to gold so that the gold can be readily recycled.

BRIEF SUMMARY OF THE INVENTION

The present invention provides a process for forming a dental prosthesis from a metallic body comprising fabricating a dental prosthesis from a metallic body comprising principally gold and at least one additional metal that in combination with the gold age hardens the alloy and is also more readily oxidized than gold. The fabrication technique is one that produces scrap metal left over from forming the dental prosthesis. Afterwards, scrap resulting from fabricating the dental prosthesis is melted in an oxidizing environment to recover substantially pure gold.

Exemplary metals alloyed with the gold in a machined dental prosthesis include titanium, zirconium, yttrium and chromium. Barium or the like may also be included for grain refining.

DESCRIPTION

Alloys suitable for practice of this invention consist essentially of gold and base metals, that is, metals that are more readily oxidized than gold. Thus, platinum group metals which do not readily oxidize are not included in the alloys. The principal base metal alloying ingredient or ingredients are those which age harden a gold alloy as well as being more readily oxidized than gold. The base metals are also biocompatible for use in the oral cavity. Examples are titanium, zirconium, yttrium and chromium.

If one considers a binary phase diagram of such an alloying element in gold, it is found that there is more solid solubility of the base metal in the gold at elevated temperatures and decreasing solubility with decreasing temperature. Commonly there are intermetallic compounds of the base metal and gold.

To age harden an alloy, it is maintained at a temperature higher than the line representing solid solubility until essentially all of the base metal is in solid solution in the gold. This does not necessarily require a reheating of the alloy, but may also occur upon cooling of the alloy from the molten state. The aging or age hardening occurs when the alloy is heated or maintained at a temperature below the solid solubility line so that the base metal segregates from a supersaturated solid solution and forms regions of intermetallic compound which interfere with deformation of the alloy, thereby increasing its hardness and strength. If the aging process is continued for a longer time (or at higher temperature), intermetallic compounds will precipitate of the alloy matrix, becoming non-coherent with the matrix crystal structure and the strengthening effect will be lost or degraded. Age hardening techniques are well known. Forming solid solutions and aging are kinetic phenomena, and the best times and temperatures for specific alloys are readily determined with only a few straightforward tests.

For example, a gold alloy with about 1.7% titanium has a solution heating cycle of about 15 minutes at 900 to 950° C. in air. If the alloy is used for a porcelain fused to a metal prosthesis, after applying the porcelain, the alloy is aged at 500° C. for about 15 minutes in air. It is believed that such a solution and aging cycle is also typical for other high-gold alloys of this invention.

Specific alloys found useful in the practice of this invention comprise principally gold with from 1 to 5% by weight of titanium, from 1 to 5% of zirconium, from 0.25 to 2% yttrium, or from 1 to 10% chromium. It is found that titanium and zirconium are effectively interchangeable on an atomic percentage basis. In other words, the hardening effect is similar for similar atomic percent content. Thus, ternary alloys of titanium and zirconium in gold may also be employed. Such an alloy would have from 0.5 to 4.5% titanium plus 0.5 to 4.5% zirconium with the total of titanium plus zirconium being in the range of from 1 to 5%. Surprisingly, the combination of titanium and zirconium in the gold alloy results in grain refinement, so that other grain refining elements may not be needed. Other ternary alloys including base metals may also be employed. Percentages stated throughout the description and claims are all percent by weight.

Some examples of suitable alloys for practice of this invention are in the following table.

| Weight Percent | | | | Atomic Percent | | | As cast |
| --- | --- | --- | --- | --- | --- | --- | --- |
| Ti | Zr | Au | Alloy | Ti | Zr | Au | VHN |
| 0 | 1.5 | 98.5 | 1 | 0.0 | 3.2 | 96.8 | 67 |
| 0 | 2.5 | 97.5 | 2 | 0.0 | 5.2 | 94.8 | 174 |
| 0.5 | 0.5 | 99 | 3 | 2.0 | 1.1 | 96.9 | 79 |
| 0.5 | 1.5 | 98 | 4 | 2.0 | 3.1 | 94.9 | 188 |
| 1.5 | 0.5 | 98 | 5 | 5.9 | 1.0 | 93.1 | 206 |
| 1.5 | 2.5 | 96 | 6 | 5.7 | 5.0 | 89.2 | 236 |
| 1.5 | 0 | 98.5 | 7 | 5.9 | 0.0 | 94.1 | 123 |
| 2.5 | 0 | 97.5 | 8 | 9.5 | 0.0 | 90.5 | 240 |

Another example of a suitable alloy is 99.5% gold and 0.5% yttrium with an as cast VHN hardness of about 90. Pure gold has a VHN of about 30.

By modifying the nature and amount of base elements, high gold alloys with differing hardness and strength can be achieved. This allows the use of these alloys in a wide range of dental prosthetic applications.

Titanium, zirconium and yttrium are desirable additions since the alloy retains very nearly the color of pure gold. In this way the color of gold is preserved while strengthening the alloy. For the traditional dental alloys, the additions of palladium or platinum that are necessary to strengthen the alloy also whiten the alloy. In practice of this invention, when a white alloy is desired, chromium additions may be used. Chromium strengthens and whitens the alloy. Such gold chromium alloys are especially suited to machining or energy beam sintering since they are difficult to cold work.

Although the alloys consist essentially of gold and the base elements listed above, it can be desirable to include up to about 0.3% barium, boron or some of the rare earth metals which act to refine grain size. Any such additions for grain refining are with metals more readily oxidized than gold. For example, iridium refines grain of high carat gold, but would not be useful since it is a platinum group metal that does not oxidize more readily than gold. Boron may also be useful although it would probably not considered a metal and despite the fact that it has been found difficult to obtain consistent or reliable grain refining results.

The lower composition limits for the base metals mentioned above are the amounts of addition where a significant age hardening effect is seen. These limits are somewhat "fuzzy" or approximate, since the amount of age hardening desired may vary from one application to another. Furthermore, the lower limits may be lower when one uses a ternary alloy to obtain an equivalent age-hardening effect. It may also occur that there are other base metals which may be included in the alloy to form ternary intermetallic compounds, for example, which provide equivalent age-hardening. The upper limits of base metal concentration mentioned above are approximately the solid solubility limits of the respective metals in gold. These limits may differ somewhat in ternary alloys equivalent to the binary alloys.

A dental prosthesis or restoration may be made from such an age-hardenable alloy by machining. First, one makes a body of the alloy by conventional melting such as in a cold crucible arc furnace or in a heated crucible in a protective atmosphere. Or, the alloy may be formed by levitation melting without contact with any crucible. Any conventional heating may be employed, including radiant heating and induction heating. Techniques for forming the body of alloy are all conventional.

The alloy is formed into a body that may be machined in the as-cast shape or a casting may be hot or cold worked, as desired, to a suitable geometry before machining. Machining may be of a body that is in the as-cast condition, hot worked, cold worked, annealed or age hardened.

When such a body is to be formed into a dental prosthesis by energy beam sintering, the initial body may be smaller than the final prosthesis and serve as a core on which powder is sintered to complete the prosthesis to the desired geometry for the specific patient.

Preferably, the body is machined to the geometry of the desired metal portion of the dental prosthesis by CAD/CAM since this is the least costly technique available. Any conventional machining may be used. The dental appliance or prosthesis made by machining may be entirely made of the alloy (i.e. with the bare metal showing), or may be a coping upon which dental porcelain is fired.

Another technique for making a dental prosthesis comprises sintering of metal powder in a high energy beam, such as a spot of light from a laser or an electron beam. The technique is known as laser sintering or rapid prototyping, and may be referred to herein as energy beam sintering. Metal powder of a suitable composition is placed on a preform or substrate and a small spot on the surface of the powder is heated by application of a focused beam having sufficient intensity to melt or nearly melt some of the powder. The powder is caused to consolidate into a solid coherent mass by localized melting, or by solid state bonding when the intensity is sufficient to nearly melt the powder. In effect, the particles of powder are welded together with or without a liquid phase.

It might be noted that such energy beam sintering of the powder causes shrinkage and consolidation so that little, if any, porosity remains in the sold body formed. Some minor porosity may not be undesirable since the surface may provide a better base for adhesion of a porcelain coating on the prosthesis. The energy beam sintering technique can be made more economical by forming the final geometry of the prosthesis on a solid core of suitable alloy, ordinarily the same alloy as the powder. Then, a layer of sintered powder is formed on the core to build up to the desired geometry. When using alloys as described herein, the sintering should be conducted in a non-oxidizing environment so that composition of the alloy powder, which has high surface area, is not changed significantly when heated. Vacuum, inert gas or reducing gas protective environments may be used.

The location of the focused spot where sintering is desired is computer controlled in a manner quite similar to CAD/CAM or NC machining. The locus of adding powder and sintering is controlled to gradually build up the solid body of sintered powder to the desired geometry of the dental prosthesis.

Although machining and rapid prototyping are the only manufacturing techniques specifically described herein, principles of this invention may be suitable for other manufacturing techniques which, by their nature, produce scrap metal having a composition similar to that of the completed prosthesis. When such techniques are used, gold in the scrap metal can be recovered easily and economically by oxidation of the base metals in the gold.

The alloys described herein are particularly well suited for application of a porcelain layer since a thin adherent oxide film is readily formed from the base metals included in the composition. Porcelain may be applied after the prosthesis is age hardened and/or the age hardening may occur during the heating cycle for applying the porcelain coating. In the event there is age hardening before application of porcelain, care should be taken that the time and temperature of age hardening are low enough that the alloy does not over-age during application of the porcelain.

If desired, the alloy may be age hardened before machining and then solution treated so that it age hardens again during application of porcelain. The choice of these techniques are well within the skill of the art. Knowledge of the time and temperature cycle for applying porcelain to the dental prosthesis and the choice of porcelain which may be used, are not necessary for a practice of this invention. As a technician knows, mostly what is desired is a coefficient of thermal expansion compatible with that of the gold alloy. Of course, other properties of the porcelain such as hardness, color, and the like are also important for the technician in the dental lab, and those are well within the skill of the art.

During the course of machining a dental prosthesis from a body of alloy, an appreciable amount of scrap is produced as the larger body is machined to the desired geometry of the prosthesis. Chips of metal are removed from the cast or wrought body from which the prosthesis is machined. When a prosthesis is fabricated by energy beam sintering or rapid prototyping, excess powder may be applied or "spilled" so that scrap metal powder can be found in the apparatus.

The scrap is accumulated, and it is not necessary to take any great care to keep different grades or compositions of scrap separated. Different compositions may be commingled since the base metals are essentially entirely removed upon subsequent processing of the scrap. The accumulated scrap of these alloys should be segregated from scrap from lost wax casting, for example, since casting alloys commonly include platinum group metals that do not oxidize more readily than gold.

The scrap is melted in air or other oxidizing environment. Techniques such as induction heating are desirable to promote stirring of molten metal to expedite oxidation of the base metals in the alloy, but any heating technique is suitable.

For most rapid oxidation of the base metals a low melting metal oxide (including boron oxide, boric acid and metal borates which might not be considered metal oxides) and/or metal halide flux is melted on the surface of the scrap during this reclamation to combine with the base metal oxides. Powdered flux is mixed with accumulated alloy scrap and when heated, the flux melts first, coating much of the metal scrap particle surfaces. The oxidative potential of such oxide fluxes is greater than air alone and expedites purification of the gold.

Cupellation could also be used for removal of base metal oxides but it is less efficient than melting with a flux and is best suited for rather small batches of metal. Cupellation may also be suitable for removing other base metals such as gallium, tin and/or indium which oxidize more readily than gold, but are not as readily removed in a flux as are the oxides of titanium, zirconium, yttrium and chromium.

An exemplary flux comprises a mixture of soda ash, borax (preferably anhydrous), silica and potassium nitrate. Other ingredients which may be used in fluxes include boric acid, boric oxide, sodium fluoride, potassium fluoride, sodium borate, potassium borate and miscellaneous silicates. The proportions may be varied to vary the oxidative potential of the flux. For example, increased oxygen compounds are preferred for expediting oxidation when the additional metal in the scrap is chromium, as compared with a lesser proportion of oxygen compounds which may be suitable when the additional metal is more readily oxidized than chromium, such as titanium, zirconium or yttrium.

The melting is continued for a sufficient time and at a sufficient temperature to substantially completely oxidize the base metals so that they are in the slag. The flux combines with the metal oxides produced and floats to the top of the molten gold as a liquid slag. After cooling, the brittle slag is removed and the remaining metal is substantially pure gold. "Substantially pure gold" does not mean that five-nines gold is produced, but that the purity of the gold remaining is commercially acceptable. Typically, this may be 99.5 to 99.9% gold. The gold thus refined can then be used in the same manner as any other refined gold.

Such scrap from fabricating a dental prosthesis may be remelted in the dental lab and/or may be traded or sold back to a vendor of dental alloys for reclamation. Likewise, a dental lab may purchase alloys and make bodies for machining from the alloy, or may purchase ready-made bodies or bars of alloy from which prostheses are machined without further processing at the lab.

It may be noted that some of the alloys mentioned above may be used in the conventional lost wax method for forming of dental prostheses. Publications have suggested a gold-titanium alloy for the lost wax casting method. It is not known that any of the other alloys used in the invention have been suggested for any method of making a dental prosthesis, either by lost wax casting or by machining.

What is claimed is:

1. A process for forming a dental prosthesis comprising the steps of:
   (i) providing a metallic alloy comprising principally gold with additions of at least one additional metal selected from the group consisting of:
   from 1 to 5% by weight of titanium, zirconium or a combination thereof,
   from 0.25 to 2% by weight yttrium, and
   from 1 to 10% by weight chromium;
   and a grain refiner that oxidizes more readily than gold provided that the grain refiner is not a platinum group metal; and
   (ii) forming a dental prosthesis from said metallic alloy, wherein said forming step comprises at least one process selected from the group consisting of machining a dental prosthesis from an alloy body formed from said metallic alloy, and forming a dental prosthesis directly by energy beam sintering of a powder formed from the metallic alloy.

2. A process according to claim 1 wherein the grain refiner is selected from the group consisting of barium, boron and grain refining rare earth metal, in an amount of up to 0.3% by weight of the alloy.

3. A process according to claim 2 wherein the at least one additional metal comprises from 1 to 5% by weight titanium.

4. A process according to claim 1 wherein the at least one additional metal comprises from 1 to 5% by weight titanium.

5. A process according to claim 1 wherein the at least one additional metal comprises at least 0.5% by weight titanium and at least 0.5% by weight zirconium, the total of titanium and zirconium being in the range of from 1 to 5% of the alloy by weight.

6. A process according to claim 1 wherein the at least one additional metal comprises from 1 to 5% by weight zirconium.

7. A process according to claim 1 wherein the at least one additional metal comprises from 0.25 to 2% by weight yttrium.

8. A process according to claim 1 wherein the at least one additional metal comprises from 1 to 10% by weight chromium.

9. A process according to claim 1 further comprising the step of:
   accumulating scrap metal from the forming step; and
   oxidizing the scrap to recover substantially pure gold.

10. A process according to claim 1 wherein the at least one additional metal is selected from the group consisting of from 1 to 5% by weight of zirconium, from 0.25 to 2% by weight yttrium, and from 1 to 10% by weight chromium.

* * * * *